United States Patent [19]

Blumenthal

[11] Patent Number: 5,048,529
[45] Date of Patent: Sep. 17, 1991

[54] ULTRASONIC TRANSDUCER PROBE

[75] Inventor: Rafael Blumenthal, Kiryat Tivon, Israel

[73] Assignee: Elscint Ltd., Haifa, Israel

[21] Appl. No.: 384,809

[22] Filed: Jul. 25, 1989

[30] Foreign Application Priority Data

Sep. 1, 1988 [IL] Israel ..................................... 87648

[51] Int. Cl.$^5$ ............................................... A61B 8/00
[52] U.S. Cl. .................................... 128/660.1; 73/633
[58] Field of Search ......................... 128/660.09, 660.1, 662.03–662.06

[56] References Cited

U.S. PATENT DOCUMENTS

| | | | |
|---|---|---|---|
| 4,362,058 | 12/1982 | Abele | 128/660.09 X |
| 4,757,818 | 7/1988 | Angelsen | 128/660.1 |
| 4,787,247 | 11/1988 | Wuchinich et al. | 128/660.1 X |
| 4,850,362 | 7/1989 | Rello et al. | 128/662.04 X |
| 4,893,628 | 1/1990 | Angelsen | 128/660.09 X |
| 4,913,158 | 4/1990 | Kikuchi et al. | 128/660.1 |

*Primary Examiner*—Francis Jaworski
*Attorney, Agent, or Firm*—Sandler, Greenblum & Bernstein

[57] ABSTRACT

A belt driven pulley mounting a transducer in a probe system used for ultrasonic medical diagnostic imaging. The location of the sector scanned by the transducer is varied by changing the angular relationship beween the drive pulley of the system and the driven pulley.

13 Claims, 2 Drawing Sheets

ULTRASONIC TRANSDUCER PROBE

FIELD OF THE INVENTION

This invention is concerned with ultrasonic medical imaging systems and more particularly with probes used in conjunction with such ultrasonic medical imaging equipment.

BACKGROUND OF THE INVENTION

The probes that are used for ultrasonic diagnostic medical imaging are often of a type that are inserted into a cavity in the patient to image organs within the cavity or juxtaposed to the cavity, hereinafter sometimes referred to as "cavital probes". These cavital probes include a transducer at an end that is inserted into the cavity and a handle at the other end. The handle end of the probe is joined to the transducer end of the probe by a stem. It is highly desirable that in such probes the transducer can be controlled to vary the center line of the arc over which the transducer scans. In normal operation the scanning arc describes a scanning sector of approximately 110 degrees. Thus, the location of the scanning sector should be movable. When the location of the scanning sector is controllably movable, then by additionally moving the probe manually within the cavity it is possible to obtain scans of almost all of the cavity organs thereto juxtaposed.

The controls for adjusting the location of the scanning sector must be small enough to fit within the probe and more particularly into the stem of the probe.

The handle portion of the probe includes the motor for moving the transducer in a scanning arc; i.e. in a reciprocating motion over an arc of approximately 110 degrees. The transducer end of the probe is usually bulbous having a window for enabling the ultransonic energy to readily pass to and from the transducer.

BRIEF DESCRIPTION OF THE INVENTION

According to a broad aspect of the present invention a cavital probe for use with ultrasonic medical diagnostic imaging systems is provided, said probe comprising:
   ultrasonic transducer means,
   motor means for driving a motor shaft over an arc,
   drive pulley means on said motor shaft and driven pulley means spaced apart from said drive pulley means,
   means for coupling said drive pulley means to said driven pulley means,
   means for attaching said transducer means to said driven pulley means to drive said transducer in a scanning mode in an arc defining a scanned sector, and
   means for changing the location of said scanned sector by varying the angular relationship between said drive pulley means and said driven pulley means.

According to a feature of the invention the means for varying the angular relationship between said drive pulley and said drive pulley comprises a pair of loops between said drive pulley and said driven pulley, and means for shortening the length of one of the loops while simultaneously increasing the length of the other loop.

BRIEF DESCRIPTION OF THE DRAWINGS

The above named and other features and objects of the present invention will be better understood when considered in the light of the following description of a broad aspect of the present invention made in conjunction with the accompanying drawings wherein.

GENERAL DESCRIPTION

Figure 1:
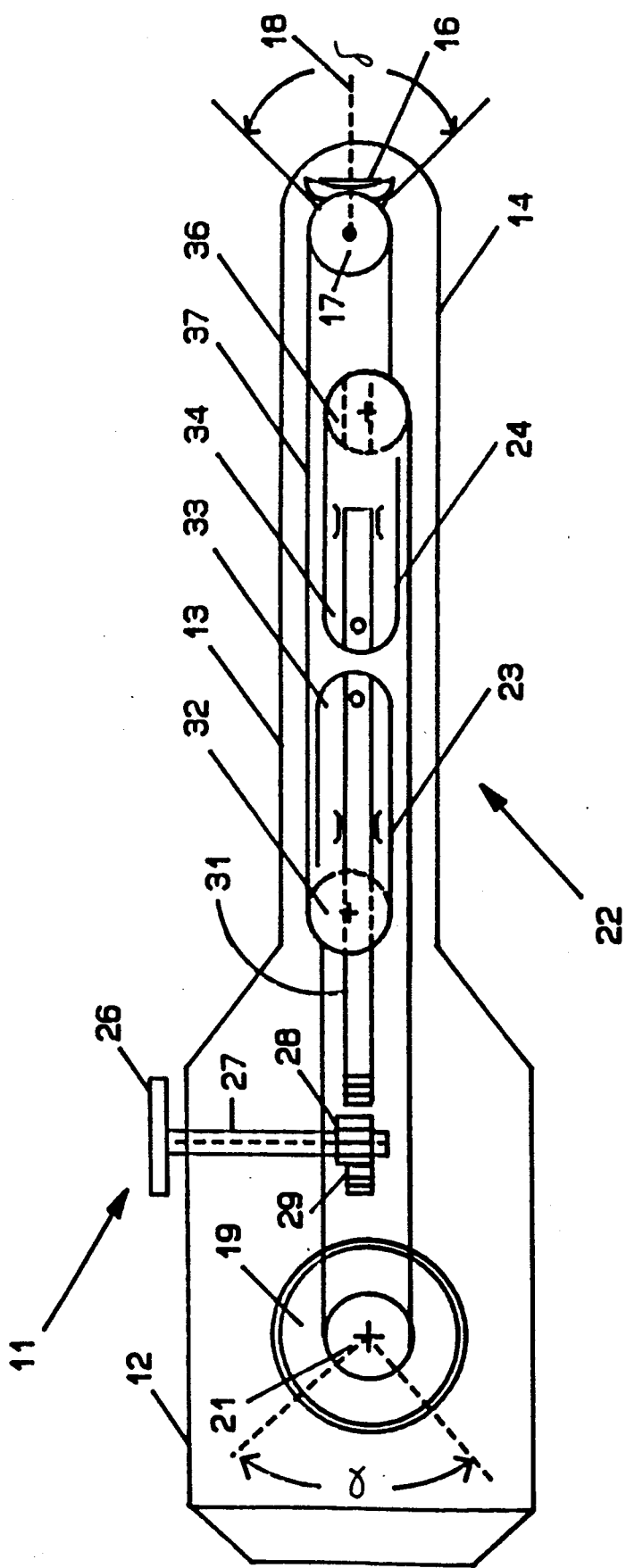
FIG. 1 is a sectional pictorial view of the inventive ultrasonic probe.

In accordance with a broad aspect of the present invention a probe 11 for use with ultrasonic medical diagnostic imaging systems is shown in FIG. 1. The probe includes a handle portion 12, a stem portion 13 which extends from the handle to the window portion 14 through which ultrasonic signals and the ultrasonic echoes readily pass.

The window portion 14 is often characterised by having a bulbous shape to accommodate the transducer 16 as it rotates on a driven pulley 17. In a preferred embodiment the motion of the transducer is reciprocating so that it scans a sector having an angle $\delta$ of 110degrees. It is desirous to be able to move the center line 18 of the scan sector defined by the angle $\delta$ so that the transducer controllably scans different sectors.

The handle portion 12 contains a drive motor 19. The drive motor preferably operates reciprocatingly over an angle $\alpha$ to cause the transducer 16 to scan over the angle $\delta$. The shaft of drive motor 19 is coupled to a drive pulley 21. The drive pulley 21 is coupled to the driven pulley 17.

Means are provided between the drive pulley 21 and the driven pulley 17 to enable changing the phase relationship between the drive pulley and the driven pulley. This means comprises intermediate pulley arrangement 22. Basically the intermediate pulley arrangement 22 comprises a pair of loops 23 and 24 between said drive pulley and the driven pulley along with means for changing the size of one of the loops 23 while simultaneously inversely changing the size of the second loop 24 of the pair of loops.

More particularly, the means for changing the size includes a knob 26 attached to a knob shaft 27 attached to a pinion gear 28. The pinion gear meshes with a rack gear 29 to controllably move slide 31. The movement of slide 31 changes the lengths of the two loops 23 and 24 by lengthening one loop and shortening the other loop proportionally, for example. Loop 23 includes a first fixed position idler pulley 32 and a first sliding position idler pulley 33. The sliding position idler pulley 33 if fixedly mounted to slide 31. Also fixed to slide 31 is the second slidable idler pulley 34. The second slidable idler pulley 34 combines with a second fixed position idler pulley 36 to form the second loop 24. The pulleys are all attached with one continuous belt 37 arranged to be non-slipping on the pulleys in a manner well known to those skilled in the art. For example, the belt is fixed positively to points on the circumferences of pulleys 21 and 17.

By moving the slide 31 towards the drive pulley 18, the first loop 23 is shortened and the second loop 24 is lengthened. Simultaneously, the driven pulley 17 is moved clockwise with respect to the drive pulley; i.e., the center line of the scanned sector is moved clockwise and the scanned sector itself, of course, is centered above the new center line position so that a different sector is scanned.

When the slide 31 is moved away from the drive pulley 21 towards the driven pulley 17 then the first loop is lengthened and the second loop is shortened and the center line of the scanned sector is moved counter clockwise; i.e., the phase of the driven pulley is moved counter clockwise with respect to the phase of the drive pulley.

Figure 2:
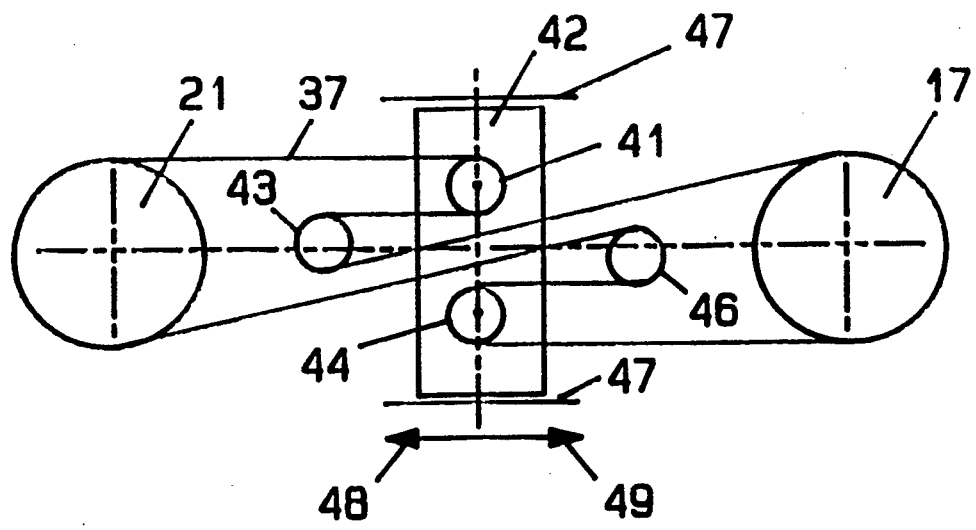
FIGS. 2-4 are different embodiments of belt and pulleys used for changing the phase of the driven pulley relative to the drive pulley even while the drive and driven pulley are in the operating mode to thereby change the location of the scanned sector.

The belt and pulley arrangement of FIG. 1 shows all of the idler pulleys almost aligned in a straight line. FIG. 2 shows an arrangement whereby the drive pulley 21 and the driven pulley 17 are inter-connected by a belt and pulley arrangement wherein the idler pulleys are not aligned. The first loop 23 is made up by the belt 37 going around a first movable idler pulley 41. The first movable idler pulley is fixedly attached to slide 42. The belt 37 then goes to a first fixed idler pulley 43 and from there to the drive pulley 17. Subsequently, it goes from the drive pulley 17 to the second movable pulley 44 and from there to the second fixed pulley 46. The second movable pulley and second fixed pulley form the second loop 24.

Due to the lack of alignment of the idler pulleys a torque is applied to the slide 42. To offset this torque a guid 47 retains the slide in its position. Means, of course, are provided although not shown for moving the slide in the direction of the arrows 48 and 49 within the guide 47.

Figure 3:
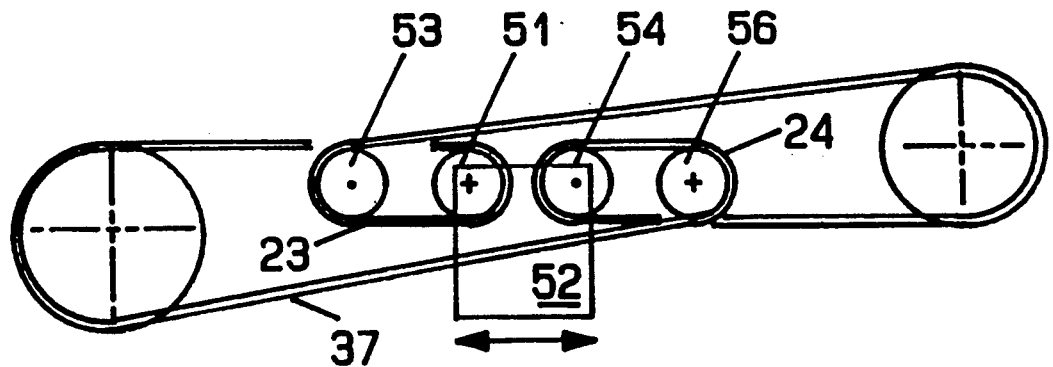

In FIG. 3 the idler pulleys are again aligned; and therefore, a guide is not required. Here again the drive pulley 21 and the driven pulley 17 are attached by belt 37 forming the first loop 23 and the second loop 24. The first movable pulley is shown at 51 mounted on slide 52. The first fixed pulley is shown as idler pulley 53. The second movable pulley is 54 in the loop 24 formed along with the second fixed idler pulley 56. Here the actuation of the slide causes the movement of the phase of the driven pulley relative to the phase of the drive pulley to be effective in much the same way as the arrangement of FIG. 1.

Figure 4:
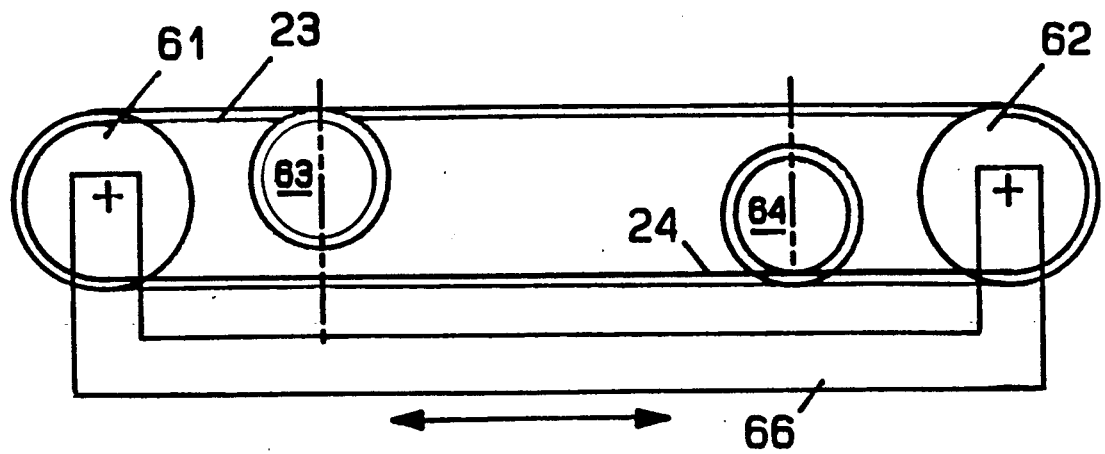

FIG. 4 shows an embodiment that eliminates the movable idler pulleys. Herein the drive pulley is shown as 61 and the driven pulley as 62. The first loop 23 surrounds a fixed idler 63. The second loop 24 surrounds a second fixed idler 64. Here the relative size of the loops are changed by moving the drive and the driven pulleys coupling bar 66 coupling the drive pulley 61 to the driven pulley 62. Means are provided (not shown) for moving the coupling bar 66 to vary the relative size of the loops 24 and 23. When the loop 24 is made shorter; i.e., when the coupling bar 66 is moved to the left in FIG. 4 then loop 23; i.e., the belt between drive pulley 61 and idler pulley 63 is made longer. When this happens then the center line of the scanned sector is moved counter-clockwise. Similarly, when the coupling bar 66 is moved to the right, then loop 23 is made shorter and loop 24 is made longer. When loop 24 is made longer then the center line of the scanned sector is rotated clockwise to change the sector that is being scanned.

When in operation a unique belted pulley arrangement is provided wherein phase of the sector being scanned by the transducer attached to a driven pulley can be selectively changed. The change is made by varying the relative size of two loops that extend between the driven pulley and drive pulley.

While the invention has been described with the use of several exemplary embodiments, it should be understood that these embodiments are by way of example only, and not as limitations on the scope of the invention, which invention is defined by the accompanying claims.

What is claimed is:

1. A probe system for use with ultrasonic medical diagnostic imaging systems, said probe system comprising:
   ultrasonic transducer means,
   motor means for driving a motor shaft through an arc,
   a drive pulley attached to said shaft,
   a driven pulley for moving the transducer means through an arc to scan a sector, said scanned sector having a center line,
   the axes of said drive pulley and said driven pulley being parallel, and said drive pulley and said driven pulley having an initial rotational angular relationship,
   means for coupling said motor shaft to said drive pulley,
   belt coupling means for coupling said drive pulley to said driven pulley,
   said belt coupling means including at least one drive idler pulley associated with and proximate to said drive pulley and at least one driven idler pulley means associate with and proximate to said driven pulley with a belt extending from said drive pulley to said at least one drive idler pulley, to said driven pulley, to said at least one driven idler pulley and back to said drive pulley.
   means for changing the intial rotational angular relationship between the drive pulley and said driven pulley to change the location of said scanned sector and the location of the center line by changing the length of the belt extending between said drive pulley and said drive idler pulley relative to the length of the belt extending between the driven pulley and the driven idler pulley.

2. The probe system of claim 1 wherein said belt means is attached to said drive pulleys and said driven pulleys in a non-slip manner.

3. The probe system of claim 2 wherein the attachment of said belt to said pulleys comprises fixing the belt positively to points on the circumferences of the drive pulley and the driven pulley.

4. The probe system of claim 1 wherein said motor means for driving the motor shaft through an arc drives the shaft in a reciprocating manner through said arc.

5. A probe system for use with ultrasonic medical diagnostic imaging systems, said probe system comprising:
   ultrasonic transducer means,
   motor means for driving the motor shaft through an arc,
   a drive pulley attached to said shaft,
   a driven pulley for moving the transducer means through an arc to scan a sector, said scanned sector having a center line,
   coupling means for coupling said drive pulley to said driven pulley,
   said coupling means including belt means,
   said coupling means including a drive idler gear system and a driven idler gear system,
   said belt means describing a pair of loops, a first loop of said pair of loops being described in conjunction with said drive idler gear system, a second loop of said pair of loops being described in conjunction with said driven idler gear system, means for changing the location of said scanned sector, and said means for changing the location of said scanned sector comprising means for changing the size of said first loop relative to said second loop.

6. The probe system of claim 5 wherein said means for changing the sizes of the loops comprises means for increasing the size of one of the loops while proportionately decreasing the size of the other loop.

7. The probe system of claim 5 wherein said means for changing the location of said scanned sector comprises slide means located between said drive pulley and said driven pulley, and means for moving said slide means to change the sizes of each of said pair of loops.

8. The probe system of claim 7 wherein said means for moving said slide means comprises a handle attached to a pinion gear, rack gear means of said slide means meshing with said pinion gear whereby rotation of said handle causes said slide to move.

9. The probe system of claim 5 wherein said first and second pair of idler pulleys are substantially aligned in a straight line between said drive and driven pulleys.

10. The probe system of claim 5 wherein said idler pulleys are on line extending between said drive and said driven pulleys, said line of idler pulleys being displaced from a line extending between the axes of said drive pulley and the driven pulley.

11. A probe system for use with ultrasonic medical diagnostic imaging systems, said probe system comprising:

ultrasonic transducer means, motor means for driving a motor shaft through an arc, a drive pulley attached to said motor shaft, a driven pulley for moving the transducer means through an arc to scan a sector, means for changing the sector scanned, belt means for coupling said drive pulley to said driven pulley, a drive idler pulley system and a driven idler pulley system between said drive pulley and said driven pulley, said drive and driven idler pulley system being characterized by being closer to either said drive pulley or said driven pulley, and said means for changing the sector scanned comprising means for varying the relative distances between said drive pulley and said drive idler pulley system and between said driven pulley and said driven idler pulley system.

12. The probe system of claim 11 wherein said drive idler pulley system comprises a first idler pulley being at a variable distance from said drive pulley and wrehin said driven idler pulley system comprises a second idler pulley being at a variable distance for said driven pulley and wherein said means for changing the sector scanned comprises means for changing the variable distances between the drive pulley and the first idler pulley and for changing the variable distance between the driven pulley and the second idler pulley.

13. The probe system of claim 11 wherein a first single idler pulley is associated with said drive pulley to form said first loop and a second single idler pulley is associated with said driven pulley to form said second loop, coupling bar means attaching said drive pulley to said driven pulley, means for moving said coupling bar means to change the size of said first loop and said second loop and to thereby change the location of the scan sector.

* * * * *